United States Patent [19]

Ruell et al.

[11] 4,358,677
[45] Nov. 9, 1982

[54] TRANSDUCER FOR FINGERPRINTS AND APPARATUS FOR ANALYZING FINGERPRINTS

[75] Inventors: Hartwig Ruell; Wolfgang Feix, both of Mt. Laurel, N.J.

[73] Assignee: Siemens Corporation, Iselin, N.J.

[21] Appl. No.: 152,513

[22] Filed: May 22, 1980

[51] Int. Cl.³ .......................... H01J 3/14; G06K 9/00
[52] U.S. Cl. .................................. 250/216; 340/825.3; 340/146.3 E; 356/71
[58] Field of Search .................. 356/71; 264/25, 40.1, 264/349, 230; 346/21, 77 E; 365/106, 126; 250/216; 340/825.3, 146.3 E; 425/508, 174.8 E, 135

[56] References Cited

U.S. PATENT DOCUMENTS

| | | | |
|---|---|---|---|
| 3,196,011 | 7/1965 | Gunther et al. | 346/77 E |
| 3,542,545 | 11/1970 | Goffe | 346/77 E |
| 3,660,818 | 5/1972 | Amodei | 365/106 |
| 3,716,359 | 2/1973 | Sheridon | 365/126 |
| 3,795,514 | 3/1974 | Jvirblis et al. | 346/77 E |
| 3,865,488 | 2/1975 | Del Rio | 340/146.3 E |
| 4,023,969 | 5/1977 | Sheridon | 346/77 E |
| 4,120,585 | 10/1978 | De Palma et al. | 356/71 |
| 4,223,062 | 9/1980 | Hession | 365/126 |

OTHER PUBLICATIONS

Spie, vol. 123 (1977) pp. 32–36, "Optical Storage Materials and Methods."

Primary Examiner—Willard E. Hoag
Attorney, Agent, or Firm—Karl F. Milde, Jr.

[57] ABSTRACT

The fingerprint transducer contains a sensing member having a sensing surface for receiving a fingerprint. The sensing member is made of a material which has a transition or softening temperature that is higher than ambient temperature and close to the temperature of the finger. Particularly, the softening temperature is chosen such that the material of the sensing member will start to melt on the surface when the finger is pressed against the sensing surface. The sensing surface has a surface relief of random roughness. In other words, the sensing surface has variations in elevation which do not show a specific pattern. The method for analyzing fingerprints comprises the steps of generating a surface relief of random space on a sensing surface of a sensing member, generating the fingerprint on the sensing surface by pressing a finger thereto, and optically reading the fingerprint from the sensing surface.

7 Claims, 12 Drawing Figures

TRANSDUCER FOR FINGERPRINTS AND APPARATUS FOR ANALYZING FINGERPRINTS

FIELD OF THE INVENTION

This invention relates to an apparatus for identification of fingerprints. In particular, this invention relates to an input transducer or input sensor for sensing a fingerprint and entering corresponding information into a fingerprint identification device. Still more particularly, this invention relates to a transducer having a surface for pressing a finger thereto. The invention also relates to a method for recording and analyzing fingerprints.

CROSS REFERENCE TO RELATED APPLICATION

This application relates to the same technical field as the commonly-owned, copending U.S. patent application of Hartwig Ruell entitled "Fingerprint Transducer and Method for Enhancing Fingerprints", Ser. No. 152,514 filed May 22, 1980, now U.S. Pat. No. 4,336,998.

BACKGROUND OF THE INVENTION

In a fingerprint input transducer or sensor, the finger under investigation is usually pressed against a flat surface, such as one side of a glass plate, and the ridge-valley pattern of the finger is sensed by some sensing means such as an interrogating light beam. The processing of the fingerprint information thus obtained may comprise laser techniques. Such fingerprint identification devices are generally used to control the access of individuals to information (information access control), for instance computer terminals, or buildings (physical access control).

One of the problems associated with fingerprint sensors concerns the reliable sensing of weak fingerprints. "Weak fingerprints" are fingerprints which have a small modulation depth on the sensing surface, or in other words, a small amount of topographic relief. A weak fingerprint may occur when the finger under test is not firmly pressed against the sensing surface, when the finger does not have sufficient fluid such as oil or moisture to leave sufficient traces on the surface, etc.

Therefore, there is a need for a fingerprint input sensor or transducer which is adapted to sense not only fingerprints of regular quality, but also weak fingerprints of small modulation depth. The transducer should be of a simple structure. There is also a need for a method for easily analyzing fingerprints.

Generally speaking the fingerprint transducer should allow for transferring the information contained in the structure of a human fingerprint into a verification terminal such that a maximum amount of information contained in the skin structure can be captured. The fingerprint transducer should work fast and be reusable after any analysis or verification attempt.

The U.S. Pat. No. 4,053,228 discloses a finger identification system in which a fingerpress is formed by pressing a finger against the back surface of a transparent glass plate and holding it in a predetermined position thereon. This fingerpress is interrogated by a light beam directed through the front surface of the glass plate. The interrogating beam is partially reflected at the back surface of the glass surface to provide a signal beam, carrying fingerpress information. The back surface of the glass plate is coated with a coating to enhance the difference in reflectivity of the valleys and crests of the fingerpress. In particular, the coating on the back surface enhances the difference in reflection at that surface between those areas where the crests of the finger are in intimate contact with the back surface of the plate and those areas under the valleys of the finger, where air is in contact with the back surface of the plate. In this fingerprint transducer an enhanced fingerpress will only be created as long as the finger engages the back surface of the plate, that is for a short while.

U.S. Pat. No. 4,120,585 discloses a pliable, resilient prism for use in an optical imaging system such as a fingerprint reader. The base surface of the prism is contacted by the finger under investigation. The pliable prism deforms under the pressure of the contacting finger. Light from a light source passes through one side face of the prism to the base surface from where it is reflected and passed through the other side face to a photosensitive element. This element is provided for actuating the optical imaging system. If there is sufficient finger pressure, an air gap will be created between the base surface and a housing, resulting in an additional area the light beam of which is directed to a photosensitive element. This element will activate the system by closing of a switch. In this fingerprint system, no means are discussed to process weak fingerprints.

In SPIE, Vol. 185, Optical Processing Systems (1979), pp. 86–92, an elastomer storage device is disclosed which uses a photoconductor. A glass substrate is chemically etched to form a transparent conductive ground plane. The ground plane is coated with the mentioned photoconductor and overcoated with a thin elastomer layer. A charge plane is positioned several mils above, and parallel to, the elastomer surface. The resulting gap is filled with low pressure argon. In operation, a high voltage source is connected between the charge plane and the ground plane, producing an electrostatic force across the elastomer and photoconductor layers. The electrostatic force is normal to the elastomer surface and is proportional to the electric field strength at each point. Because the elastomer is incompressible and the force is uniform, no deformation occurs. When the photoconductor is exposed to a light distribution, charge carriers are photogenerated and move in the electric field to the elastomer-photoconductor interface where they are trapped. The trapped charges form an electrostatic surface charge layer in which the charge density distribution is directly proportional to the exposure distribution of the input signal. The resulting electric field distribution causes the elastomer to deform creating a surface relief pattern which is directly related to the exposure distribution through the surface charge density. The deformation will continue as long as the non-uniform charge distribution is maintained. This storage device, incidently, is not contemplated for use as a fingerprint transducer.

In SPIE, Vol. 123, Optical Storage Materials and Methods (1977), pp. 32–36, a thermoplastic data storage medium is disclosed. This medium is a multilayered device consisting of a thermoplastic layer, a photoconductor layer, and a transparent conductive layer coated on a glass or flexible polyester substrate. The optical data storage in thermoplastic is based on the principle that thermoplastic deforms under stress when heated to an appropriate temperature. During writing, a uniform charge is applied to the thermoplastic surface. The device is then exposed to an optical pattern which alters the conductivity of the photoconductor and thus the surface charge distribution. This non-uniform charge distribution results in electrostatic forces which deform the thermoplastic upon heating to a critical softening-/developing temperature. When the sample cools, the deformation corresponding to the optical pattern remains and the information can be retrieved by illumination with a read out beam. Also this storage medium is not contemplated for use as a fingerprint transducer.

Similar optical recording and storage devices are known from SPIE, Vol 123, Optical Storage Materials and Methods, (1977), pp. 1–16, and pp. 74–77.

BRIEF DESCRIPTION OF THE INVENTION

1. Objects

It is an object of the present invention to provide a fingerprint input sensor or transducer of simple structure which is capable of detecting and sensing a considerable amount of information contained in the skin structure of a human finger tip.

It is another object of this invention to provide a fingerprint transducer which works fast and which can be reused after an anteceding fingerprint investigation.

It is another object of this invention to provide a fingerprint transducer wherein a fingerprint can be stored for a certain period of time.

It is still another object of this invention to provide a fingerprint transducer wherein a fingerprint can be read out optically either in transmission or in reflection.

It is still another object of this invention to provide a method or process for analyzing a fingerprint which is applied to a surface.

2. Summary

According to this invention, the fingerprint input transducer contains a sensing member which has a sensing surface for receiving a fingerprint. The sensing surface has a surface relief of random roughness. In other words, there are variations in elevation on or of the surface (=relief) which have no specific pattern (=random). That is, there is a plurality of elements or points satisfying a specified geometric postulate, namely a random distribution across the sensing surface. These elevations, elements or points are preferably of the same material as the sensing member. They are small as compared to the fingerprint. Their size is such that a considerable scattering of light can be observed when the surface is illuminated. The sensing member is made of a material which has a transition or softening temperature higher than ambient temperature and close to the temperature of the finger or human body. Particularly, the softening temperature is selected such that the member material will start to melt when the finger is pressed to the sensing surface. This melting process is due to the pressure and/or the heat exerted to the surface by the finger. Generally, the softening temperature of the sensing member should be about or above 40° centigrade. Preferably, it should be within a few degrees centigrade of the temperature of the human body.

The sensing member may be made of an elastic or resilient material. Preferably it is made of an elastomer or a thermoplastic material, for instance a plasticized polystyrene. It may also be made of a material the properties of which are similar to those of an elastomer. An elastomer is any of those various polymers having the elastic properties of natural rubber. In particular, an elastomer of a comparatively low softening temperature may be chosen. Thermoplastics are polymers capable of being repeatedly softened (melted) by heat and hardened by cooling. Typical thermoplastics are polyethylene, polypropylene, polystyrenes, polyacrylics, polyvinyls, nylons and fluoropolymers.

In order to extinguish a fingerprint on the sensing surface and to randomize the relief, there may be provided a device for generating an electrostatic charge on the sensing surface, and a heating device for heating the sensing surface of the sensing member up to a temperature which is at least the softening temperature of the material of which the sensing member is made.

The charge mentioned above may be preferably applied to the surface by corona charging. For this purpose, the charging device may contain a wire which is arranged at some distance from the surface of the sensing member, and a voltage source for supplying a DC voltage between the wire and the surface of the sensing member. The charging device may also comprise an areal electrode in the shape of a wire-lattice which is located close to the surface of the sensing member, and a voltage source for applying a DC voltage between the electrode and the sensing member.

The heating device mentioned above may be an electric heating device. It may contain a heating resistor, which is, for instance, a resistance wire, an areal wire-lattice or a transparent electrode having some appropriate area-resistance. When activated, a heating current will flow through the heating resistor. The wire-lattice may be transparent with regard to the wavelength of a sensing light beam. In order to achieve good heat coupling, the heating resistor may be attached to the sensing member.

However, the heating device does not need to be an ohmic or resistive heating device. Heating can also be performed by radiation. For instance, heat can be transferred to the sensing surface by means of an infra-red (IR) laser, particularly an IR LED, by means of a semiconductor laser or by similar IR light sources.

The fingerprint information stored in the sensing member may be read out either by optical means such as by total reflection or by laser optics, in a well-known manner. The topographic relief can be analyzed in any manner which is well known in the art.

In operation of the input transducer, in a first step, a surface relief of random roughness and of random orientation is created on a sensing surface of a sensing member. Then, in a second step, the finger under investigation is pressed against the surface of the sensing member so that it leaves behind a surface relief. Due to the temperature and the pressure of the finger the random surface relief will melt locally, preferably in places where the crests of the finger contact the sensing member. In these places, the random distribution of the elevations is disturbed. As a consequence, the molten parts will no longer scatter light in the same way as the undistrubed surrounding. This means that the fingerprint can easily be read from the transducer by optical means.

In order to extinguish the relief, the sensing surface is heated while electrostatically charging the surface. Subsequently, the surface is cooled down below the softening temperature. For instance, heating current may be sent through a heating resistor which is thermally coupled to the elastomer. By heating the sensing surface, the surface will become soft, and the melting surface will be flattened due to surface tension. However, due to the charging, a randomized relief will be created. The transducer will thus be prepared for a new fingerprint identification cycle.

One of the advantages of the present invention is that the enhanced relief on the surface of the sensing member will remain stable or "frozen in" after the finger has been pressed against the sensing surface.

The foregoing and other objects, features and advantages of the invention will be apparent from the following more particular description of the preferred embodiments of the invention, as illustrated in the accompanying drawings.

DETAILED DESCRIPTION OF THE PREFERRED EMBODIMENTS

Figure 1:
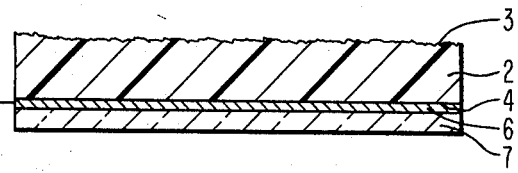
FIG. 1 is a cross-section of an embodiment of a fingerprint transducer according to the invention.
Figure 3:
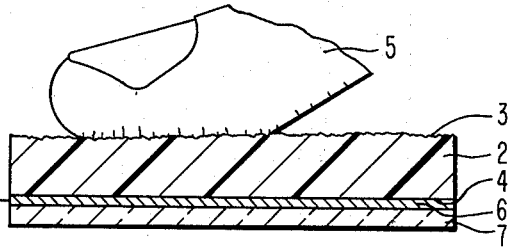
FIG. 3 is a cross-section of the fingerprint transducer according to FIG. 1, showing a finger pressed to the sensing surface.

According to FIG. 1, a rectangular flat plate is provided as a sensing member 2. The sensing member 2 has a first or sensing surface 3 and a second or lower surface 4. The sensing member 2 is made of a material, which is reusable, preferably of an elastomer or a thermoplastic material such as plasticized polystyrene. The material of the sensing member 2 is electrically non-conductive. It is chosen such that its transition or softening temperature is higher than ambient temperature surrounding the member 2, and close to the temperature of the human body. Particularly, the softening temperature should be chosen to be more than about 40° centigrade. It may be chosen to be only a few degrees centigrade above ambient temperature. The sensing surface 3 is designed to receive, for a short period of time, the pressure of a finger 5 (shown in FIG. 3) under investigation. Generally speaking, the softening temperature is selected such that a thin layer of the material on the sensing surface 3 will start to melt when the finger 5 is pressed thereto.

As a variation from the structure illustrated in FIG. 1, the sensing surface 3 of the sensing member 2 does not need to be flat. It may also be curved in such a way as to match the outline of the finger 5.

Attached to the second surface 4 is an electrode 6. The electrode 6 is preferably made of a material which is transparent with regard to the light of an interrogating beam (shown in FIGS. 5 and 6). It may be made of indium oxide (InO). The electrode 6 is in the form of a thin rectangular plate or wire system or may be a thin film coating. The electrode 6 may be connected to ground. It is supported by a light transparent supporting plate 7, for instance a glass substrate.

Figure 2:
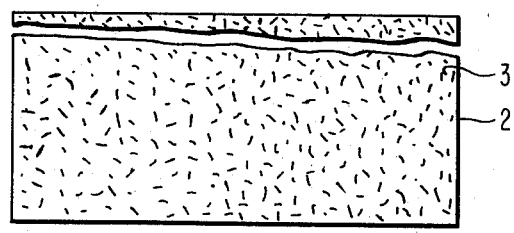
FIG. 2 is a top view of the fingerprint transducer according to FIG. 1, showing a random elevation distribution on the sensing surface.

According to FIGS. 1 and 2, the sensing surface 3 has a surface relief of random roughness. In other words, the surface 3 contains many small elevations and/or valleys in a random distribution. These variations in the elevation in or on the surface, which have no specific pattern, can be generated preferably in a way more fully described below. If the surface 3 would be exposed to light, all segments would scatter the light in a random way so that no preferred scattering direction would result. Generating a thin surface relief of random roughness is a first operational step.

In a second operational step, the finger 5 is pressed against the flat sensing surface 3 of the sensing member 2. This can be seen in FIG. 3.

Figure 4:
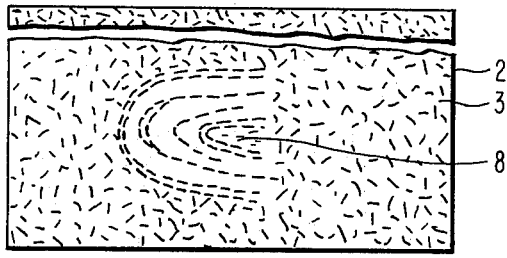
FIG. 4 is another top view of the fingerprint transducer according to FIG. 1 showing a fingerprint on the sensing surface.

The next operational step is to remove the finger 5 from the sensing surface 3. As is illustrated in FIG. 4, a fingerprint 8 is left behind on the surface 3. Due to the pressure and the temperature exerted onto the surface 3 by the "hills" of the finger, the random surface relief melts locally. In the molten segments neither elevations nor valleys exist any longer. These segments are "ironed out"; they are now flat areas.

Figure 5:
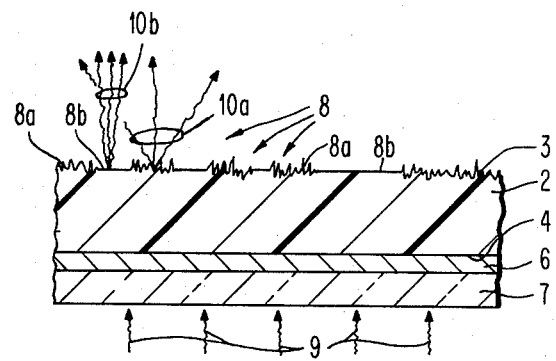
FIG. 5 is a partial and enlarged cross-section of the fingerprint transducer according to FIG. 4, showing rippled elements and flat elements on the sensing surface, where the fingerprint was made.

This is illustrated in FIG. 5. Areas or segments where still a statistical distribution is present are desigated as 8a, and areas or segments where the statistical distribution of small valleys and/or elevations has been "ironed out" by the "hills" of the finger are designated as 8b.

Figure 6:
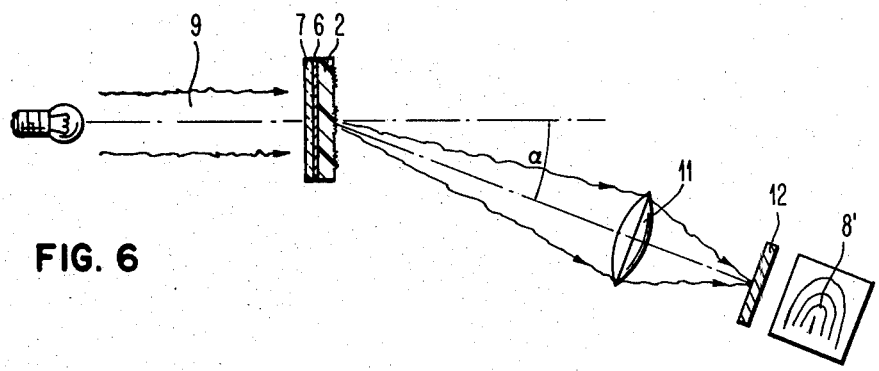
FIG. 6 is an arrangement of retrieving or reading the fingerprint.

In FIGS. 5 and 6 are shown the next operational step. In this step, the information contained in the "frozen in" fingerprint 8 is read out optically and analyzed. This can be performed by light of an interrogating or reading beam 9 either in transmission or reflection. The embodiment of FIGS. 5 and 6 shows reading out by aid of transmitted light. The beam 9 is directed perpendicularly to the lower surface 4 of the sensing member 2. For this purpose the beam 9 is transmitted through the transparent member 7 and the transparent electrode 6 into the sensing member 2. Finally it arrives at the upper surface 3. After having passed the fingerprint 8 it carries the fingerprint information. In accordance with the valleys and ridges of the surface 3, the light is spatially modulated, that means it carries the information about the geometrical structure of the fingerprint 8. Analyzing of the information contained in the modulated light may principally be performed in any way known in the art. FIGS. 5 and 6, however, illustrate a very simple method.

In the segments 8b, light is scattered only into narrow cones 10a surrounding the optic axis of the illuminating beam (forward scattering). In the segments 8a, however, where the random distribution of the original surface relief has not been changed by the "hills" of the finger tip, the illuminating beam is scattered into wide open cones 10a. That means that the molten parts of the member 2 no longer scatter light in the same way as the undisturbed surroundings. According to FIG. 6, if the surface 3 is observed under an oblique angle α with respect to the normal, the fingerprint pattern can be seen as dark lines on a bright background. The image of the sensing surface 3 and the image 8' of the fingerprint 8 can be directed via an optical system 11 to a light sensitive device 12. This device 12 may be an areal photoelectrode for transforming the image into electrical signals.

Figure 7:
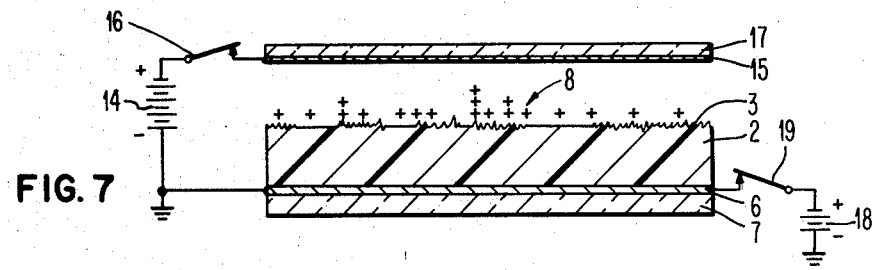
FIG. 7 is an apparatus for extinguishing the fingerprint and regaining a spatial randomized relief.

As illustrated in FIG. 7, the next step in the operation will reset the fingerprint sensor into its original status. This step comprises electrostatic charging and simultaneously heating. For this purpose, an electrostatical charging device and a heating device are provided. The charging device contains a voltage source 14 having a high voltage V which can be connected electrically between ground and an electrode 15 by means of a switch 16. The electrode 15 is arranged in some distance from the sensing surface 3. It is carried by a carrying member 17, for instance a glass substrate. The electrode 15 may be a single wire which is arranged parallel to the surface 3. In the present embodiment it is a plane electrode which is connected to the lower surface of the carrying member 17.

As soon as the switch 16 is closed, the high voltage V between the electrodes 6 and 15 will cause ionization of the air close to the electrode 15. Due to the ionization of the air, electrical charges will be directed to the sensing surface 3. These charges are retained on the surface 3. They cannot flow away from the surface 3, since the sensing member 2 is an electrical insulator.

As also illustrated in FIG. 7, the positive terminal of the high voltage source 14 is connected to the electrode 15, whereas the negative terminal is connected to the electrode 6. Therefore, the surface 3 is charged with positive particles. However, charging with negative particles is also possible. To obtain negative electrostatic charging, it is necessary only to reverse the polarity of the high voltage source 14 with regard to the electrodes 6 and 15. As indicated in FIG. 7, without heating the positive particles would preferably gather at certain surface elements in the region of the fingerprint 8. Due to the locally varying charge density, different electrical field strengths would be present, and different electric forces would be exercised on different surface elements.

Illustrated in FIG. 7 is also a heating device which in the present embodiment is of electrical nature, particularly a resistive heating device. The heating device contains a heating current source 18 and a switch 19. The heating current source 18 and the switch 19 are connected in series between the one end of the electrode 6 and ground. The other end of the electrode 6 is also connected to ground. By closing the switch 19, the heating current source 18 will emit a heating current (d-c or pulsed) that flows through the electrode 6. Thus, the electrode 6 is not only a high-voltage electrode used for electrostatically charging, it is simultaneously a heating resistor, for instance a resistance grid. The heating current will heat the sensing member 2. The value of the heating current is such as to achieve a temperature on the sensing surface 3 which is at least approximately the softening temperature of the elastomer or the thermoplastic material. In the course of the heating process the surface 3 of the sensing member 2 will become soft and start to melt. Now the surface 3 can become flat and the fingerprint 8 is extinguished. The electrostatical charge will randomly distribute on the surface, thereby exercising electrostatical forces on the surface 3 which will result in a random distribution of valleys and/or elevations. As a result, again a transducer is obtained having statistical surface properties. This effect is known in literature as Frost-effect of thermoplastic media.

Figure 8:
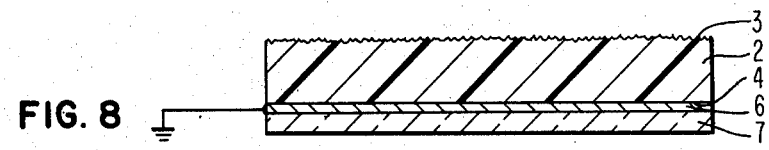
FIG. 8 is a cross-section of a fingerprint transducer ready for the next examination.

According to FIG. 8, the last operational step is cooling down the sensing member 2. This can be achieved simply by switching off the switch 19, provided that the ambient temperature is low enough. In addition, some cooling device (not shown) such as thermoelectric Peltier elements may be connected to the sensing member 2. Cooling down of the sensing member 2 results in a "freezing in" of the random pattern relief of the surface 8. It should be noted that during the cooling down operation the electrode 15 is switched off from the high voltage source 14. After cooling down, the sensing member 2 is ready for the next fingerprint processing and reading cycle.

Figure 9:
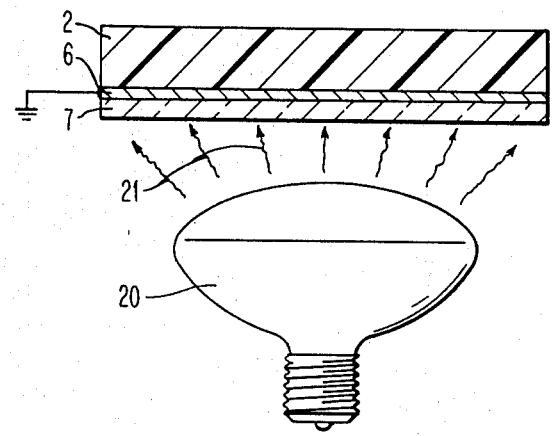
FIG. 9 shows a fingerprint transducer according to the invention which can be heated by an IR light source.

FIG. 9 illustrates that the heating of the sensing member 2 (see FIG. 7) can also be obtained by a radiation heating device. In this case, an IR radiation source 20 is used which emits IR radiation 21 towards the lower side of the electrode 6. The IR source 20 may be a single IR source or an array of single IR sources. As IR source 20, an IR emitting LED or an IR bulb may be used.

Figure 10:
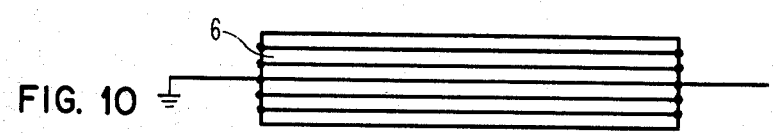
FIG. 10 shows a top view of an electrode which can be used in a transducer according to the invention.

In FIG. 10 is illustrated an embodiment of the electrode 6. The electrode 6 may be an array of parallel resistance wires. These wires may serve as well as electrode in the electrostatic charging process as a heater in the heating process.

Figure 11:
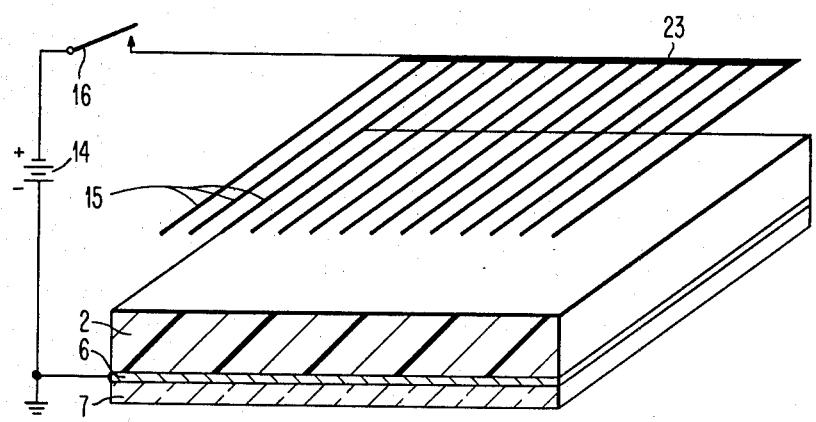
FIG. 11 shows a perspective view of an embodiment of the invention having a grid-type charging electrode.

In FIG. 11 is illustrated a perspective view of another embodiment of the invention. In this embodiment, the electrode 15 for charging the upper surface of the member consists of an array of parallel wires which are connected on one side to a connector 23 which in turn is connected via the switch 16 to the high-voltage source 14. The array of parallel wires may be retained by some suitable device (not shown).

Figure 12:
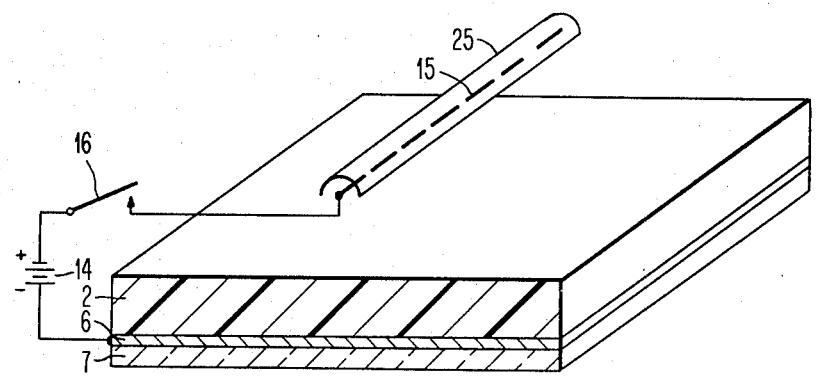
FIG. 12 shows a perspective view of another embodiment of the invention having a single wire as a charging electrode.

In FIG. 12 is shown a perspective view of still another embodiment of the invention. In this embodiment, the electrode 15 is a single wire which is retained parallel to the surface of the member 2. The electrode 15 is screened away from the surface 3 by a screen 25. Therefore, charged particles are generated substantially between the screen 25 and the upper surface 3 of the sensing member 2.

While the form of the fingerprint transducer and the method for analyzing fingerprints herein described constitute preferred embodiments of the invention, it is to be understood that the invention is not limited to these precise forms of assembly and steps, and that a variety of changes may be made therein without departing from the scope of the invention.

What is claimed is:

1. In an apparatus for the identification of fingerprints having a fingerprint sensing member with a sensing surface and means for interrogating the sensing surface with a light beam, whereby the light beam is modulated in accordance with the structure of the fingerprint, the improvement comprising the sensing surface having a random surface roughness and being made of a material having a softening temperature greater than ambient temperature and close to human body temperature such that when a finger is placed onto the sensing surface, portions of the material will soften to disturb the random surface roughness in accordance with the geometrical structure of the print of the finger, the roughness of disturbed portions of the sensing surface serving to scatter light differently from the roughness of the undisturbed portions.

2. Apparatus according to claim 1, further comprising means for generating an electrostatic charge on said sensing surface, and means for heating said sensing surface of the sensing member to a temperature which is at least the softening temperature of said material of which the sensing member is made, whereby a fingerprint on said sensing surface may be extinguished and said relief may be randomized by heating said surface and simultaneously generating said charge.

3. Apparatus according to claim 1, wherein said sensing member is a flat plate having first and second sides, which are substantially parallel, wherein said first side is said sensing surface; and further comprising an electrode attached to said second side, said electrode being at least partially transparent to the interrogating beam of light.

4. Apparatus according to claim 1, wherein the material of said sensing member is an elastomer.

5. Apparatus according to claim 4, wherein said elastomer is a plasticized polystyrene.

6. Apparatus according to claim 1, wherein said material is transparent with regard to said light beam, and further comprising a light sensitive device arranged behind said sensing member and oblique to the normal of said sensing surface for forming an image of said sensing surface.

7. Apparatus according to claim 6, wherein said light sensitive device is an areal photoelectrode for transforming said image into electrical signals.

* * * * *